United States Patent [19]

Holmgren et al.

[11] Patent Number: 4,888,275

[45] Date of Patent: Dec. 19, 1989

[54] DIAGNOSING AND MONITORING CANCER

[76] Inventors: Jan R. Holmgren, Stotekarrsvagen 11D, S-421 77 Vastra Frolunda; Leif Gustav Lindholm, Postlada 5603, S-430 31 Kullavik; Lars T. Svennerholm, Fotbollsgatan 9, S-431 39 Molndal, all of Sweden

[21] Appl. No.: 123,377

[22] Filed: Nov. 20, 1987

Related U.S. Application Data

[63] Continuation-in-part of Ser. No. 735,324, May 17, 1985.

[30] Foreign Application Priority Data

May 18, 1984 [SE] Sweden ............................ 8402702

[51] Int. Cl.$^4$ .................. G01N 33/574; G01N 33/577
[52] U.S. Cl. .......................................... 435/7; 436/64; 436/578; 436/543; 436/548; 436/813
[58] Field of Search .................. 435/7; 436/64, 518, 436/543, 548, 813; 424/3

[56] References Cited

U.S. PATENT DOCUMENTS

| | | | |
|---|---|---|---|
| 4,455,380 | 6/1984 | Adachi | 436/504 |
| 4,725,557 | 2/1988 | Miyauchi et al. | 436/543 |
| 4,757,003 | 7/1988 | Matsumoto et al. | 435/7 |

OTHER PUBLICATIONS

E. H. Holmes et al., *Journ. Biol. Chem.*, 257, 7698–7703, 1982.

Primary Examiner—Sam Rosen
Assistant Examiner—David A. Saunders
Attorney, Agent, or Firm—Darby & Darby

[57] ABSTRACT

This invention relates to the use of a specific carcinoma associated antigen/hapten of carbohydrate nature, fucosylsialosylgangliotetraose-IV$^2$-Fuc$\alpha$-II$^3$NeuAc$\alpha$-GgOse$_4$ (Lipid Document, 1977) and defined derivatives, as well as to the use of antibodies against this antigen or its derivatives for body treatment procedures related to human cancer (exemplified by small cell carcinomas of the lung).

8 Claims, 1 Drawing Sheet

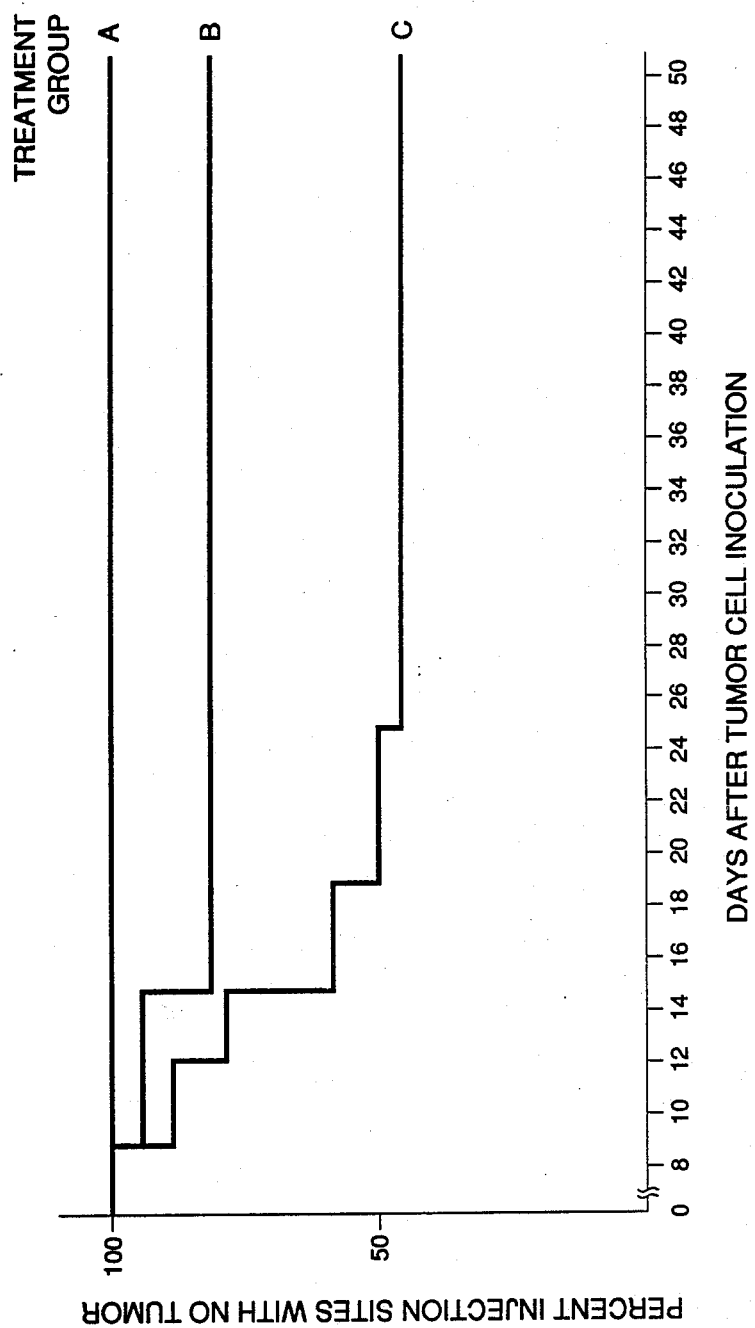

DIAGNOSING AND MONITORING CANCER

This application is a continuation-in-part of U.S. Pat. application Ser. No. 735,324, filed May 17, 1985.

FIELD OF THE INVENTION

This invention relates to the use of a specific carcinoma associated antigen/hapten of carbohydrate nature, fucosylsialosylgangliotetraose-$IV^2Fuc\alpha$-,$II^3$-NeuAc$\alpha$-GgOse$_4$ (IUPAC-IUB Lipid Document, 1977) and antibodies against this antigen for diagnostic or therapeutic procedures related to human cancer (e.g. small cell lung carcinomas) with election of Invention II Body treatment with antigens or antibodies.

BACKGROUND

It is well established that the transformation of normal tissue cells to tumor cells is associated with a change of carbohydrate structures (glycoconjugates) on the cell surface. These new or modified glycoconjugates may serve as antigens and may then represent a type of so-called tumor-associated antigens. The cell surface carbohydrates are linked either to a lipid moiety, in which case they are called glycolipids, or to peptides (proteins), in which case they are called glycopeptides (glycoproteins).

Tumor-associated glycoconjugate antigens are previously known in relation to human cancer disease. In melanomas the carbohydrate structures disialosylgangliotetraose and disialosyllactose have been identified linked to a lipid portion. Two carcinoma associated antigens CEA (carcinoembryonal antigen) and GICA (gastro-intestinal cancer antigen) have been demonstrated particularly in gastrointestinal carcinomas while a third antigen, CA-50, seems to have a more general distribution. All the antigens are shedded from the cell surface or secreted from the tumor cell and can be demonstrated in blood serums by means of immunological methods.

The present invention is based on the discovery that patients with certain forms of lung cancer (small cell carcinomas or oat-cell carcinomas) express in the primary lung tumor and its metastases an acidic glycolipid, which is not expressed in normal lung tissue. This glycolipid antigen is a ganglioside with the complete chemical structure Fuc$\alpha$1-2Gal$\beta$1-3GalNAc$\beta$1-4(NeuAc$\alpha$2-3)Gal$\beta$1-4Glc or $IV^2$Fuc$\alpha$-,$II^3$NeuAc$\alpha$-GgOse$_4$ with the short designation Fuc-GM1 (IUPAC-IUB Lipid Document, 1977). This ganglioside was first isolated from bovine brain (Ghidoni et al., J. Neurochem. 27, 511–515, 1976) but indications for its occurrence in other mammalian organs as adipose tissue, spleen and testis have also been presented. Hakomori and co-workers (Baumann et al, Cancer Res. 39, 2637–2643), 1979) isolated from rat hepatomas a ganglioside, which was tentatively identified as Fuc-GM1. A definitive establishment of the chemical structure of this ganglioside was performed by Svennerholm and collaborators (Fredman et al., Eur. J. Biochem. 116, 553–564) on gangliosides isolated from porcine nervous tissue. They also showed that chronic chloroquine treatment of the pig caused an increased lysosomal storage of Fuc-GM1 in nervous tissue (Klinghardt et al., J. Neurochem. 37, 897–908, 1981) but also in several other organs (Fredman et al., Biochem. J. 201, 581–588, 1982). Although this ganglioside has a wide distribution in pig, we have not been able to show its occurrence in normal human lung tissue or in carcinomas from a large number of human organs. In patients, died in lung small cell carcinoma, all lung tumors contained Fuc-GM1 ganglioside, and in other patients Fuc-GM1 was shed to blood serum. With the assay method for Fuc-GM1 developed by us the tumor antigen was detected on the blood serum in patients with lung small cell carcinoma but not in the blood serum of a control population or of patients with other forms of cancer.

Within the scope of the present invention procedures have been elaborated for the isolation of the tumor associated glycolipid, fucosylsialosylgangliotetraosylceramide with the short designation, ganglioside Fuc-GM1, in pure form from human cancer tissue and from animal organ. The purified ganglioside has by a special device obtained an increased immunogenic activity and then been used for the production of monoclonal antibodies. Procedures have, within the scope of the invention, been developed for the identification and quantitative determination in tissues, tissue sections, cytological preparations and various body fluids. All of these methods for diagnostic purposes are based on the fact that the antigen can be detected and quantitatively determined by the reaction with specific antibodies produced against the pure ganglioside antigen, Fuc-GM1.

The following non-limiting examples illustrate the various sources where the ganglioside antigen can be measured: surgical or autopsy material of lung, liver, brain or similar organs, cytological specimens obtained by biopsy of lung or other organs, cytological specimens obtained by biopsy of lung or other organs, where signs of cancer metastases can be suspected, cells, obtained by aspirations of the respiratory tract, expectorations, or by puncture of pleural or abdominal cavity, biological fluids like whole blood, blood plasma or serum, lymph, cerebrospinal fluid, urine, saliva or similar.

The antigen which is used in the present invention is termed, fucosylsialosylgangliotetraose and has the following chemical structure: Fuc$\alpha$1-2Gal$\beta$1-3GalNAc$\beta$1-4(NeuAc$\alpha$2-3)Gal$\beta$1-4Glc or $IV^2\alpha$Fuc1-$I^3\alpha$NeuAcGgOse$_4$ (IUPAC-IUB Lipid Document, 1977). Within the scope of the present invention all antigens, which have been modified by the removal of the terminal glucose moiety or by the substitution of the sialic acid (NeuAc) moiety to the N-acetylgalactosamine (GalNAc) moiety instead of to the galactose (Gal) moiety are covered by this patent application. The monoclonal antibodies referred to in the present invention have all been produced from antigens bound to a lipid group (acylsphingosine) but this claim will also include the binding of the antigenic group to every other compound.

The antigen which has been used in the present invention can be isolated from tumor tissue, obtained by surgery or autopsy of patients with lung small cell carcinoma. The concentration of the antigen in the tumor tissue is in general relatively low, particularly when the patient has been treated with cytostatic drugs, and the isolation of the antigen will then be laborious. We have also found another biological material, which can be used for the isolation of the cancer antigen. When a certain strain of miniature pig is foddered with chloroquine in the diet during 3–6 months, high concentrations of the ganglioside antigen is formed in the pig's central nervous system, particularly in the dorsal root ganglia. The cancer associated ganglioside antigen can then be relatively simply isolated from brain and dorsal root ganglia. By this device one is not limited for the isolation of the antigen to surgery or autopsy material and a large number of practical and ethical difficulties are avoided.

It has previously been found that gangliosides—it means glycolipids containing sialic acid—are poor immunogens and it has been difficult to produce antibodies with high affinity and specificity against them. This difficulty has been circumvented in the present invention by the adsorption of the ganglioside antigen to a bacterial membrane with known high immunogenic activity. By this device a large number of monoclonal antibodies with high specificity and affinity against the cancer antigen have been produced.

The present invention concerns in accordance herewith a procedure for the induction of the cancer associated antigen fucosylsialosylgangliotetraose in the nervous system of a particular type of miniature pig, isolation of the antigen with chromatographical methods and production of monoclonal antibodies against the purified antigen adsorbed to a certain bacterial membrane. The invention includes also the use of the compound fucosylsialosylgangliotetraose and all the derivates of this substance and all types of antibodies directed against them for the diagnosis of different cancer forms, specially certain forms of lung cancer.

It has previously been reported that monoclonal antibodies against certain tumor-associated antigens can suppress tumor development of human tumors implanted in nude mice and clinical studies in patients have also suggested the possibility to suppress or slow down tumor growth in humans (e.g. Herlin, D and Koprowski, H, PNAS (USA), 79:4761–4765, 1982; Adams, D O et al, PNAS (USA) 81:3506–3510, 1984; Sears, H F et al, Lancet I:762–765, 1982). In some of these investigations as well as in other studies, monoclonal antibodies and polyclonal antisers against tumor-associated antigens, in conjunction with macrophages and/or the complement system, have also been found to kill tumor cells in vitro. In no instance, however, has the use of antibodies directed against fucosylsialosylgangliotetraose antigen, which is the subject matter of this invention, been described for any such purposes. Likewise, neither has the fucosylsialosylgangliotetraose antigen been used to induce protective anti-tumor immunity, or antibodies against this antigen been described for detection and localization of tumors using "imaging" techniques which are otherwise obvious possible applications for tumor-associated antigens and tumor-specific antibodies, respectively (e.g. Holmgren J, ed., Tumor marker antigens, Studentlitteratur/Chartwell-Bratt Ltd, Lund, Sweden/Bromley, England, 1985). The present invention also specifically concerns the use of the compound fucosylsialosylgangliotetraose and all the derivatives of this substance and all types of antibodies directed against them for the treatment of small cell lung cancer and other human cancer disease in patients. Such use of the antibodies and antigens in question also extends to the in vivo search for and localization of Fuc-GM1 containing cancers in patients using "imaging" techniques, and the prevention of Fuc-GM1 containing human cancers by stimulating the formation of protective anti-tumor immunity in an individual.

EXAMPLE 1

Isolation of Fucosylsialosylgangliotetraose Antigen in the form of Fuc-GM1 Ganglioside from Miniature Pig, type Göttingen Chloroquine treatment of pig Miniature pigs, type Göttingen, with a weight of 20–30 kg, were given a diet, in which the regular fodder was supplemented with 30 g chloroquine diphosphate per kg fodder. The different ingredients were mixed under the addition of water and after careful mixing the fodder was pelletted and dried. The pigs were given this fodder for 2 months and were then slaughtered (bleeding under narcosis). The whole nervous system was collected, including retina and dorsal root ganglia. Brain and dorsal ganglioa + retina were processed separately, since dorsal ganglia and retina had approx. 20 times higher concentration of Fuc-GM1 than brain.

Extraction of gangliosides from tissue

The tissue was homogenized after the addition of 3 volumes of water to one volume of tissue material. After homogenization with a knife homogenizer at 1500 rpm during 3 min., 10 volumes of methanol was added under continuous stirring. Then 5 volumes of chloroform were added. After extraction for 1 h the clear supernatant was isolated by centrifugation at 2000 rpm. To the supernatant was added water to give a final chloroform-methanol-water ratio 4:8:5.6 (by volume). After mixing in a separatory funnel, two distinct phases appeared. The upper phase was collected and evaporated to dryness after the addition of 0.1 volume of butanol to prevent foaming. The evaporation was performed with a rotatory evaporator under gentle warming on a water bath, the temperature not exceeding 50° C. The residue was added 0.5 volume methanol per volume original tissue and 0.5 volume of 1.0 M potassium hydroxide and was left overnight at room temperature. The alkaline solution was neutralized to pH 8 with 1.0 M hydrochloric acid and was then allowed to dialyse against running tap water for 48 hours.

Isolation of a monosialoganglioside fraction by anion exchange chromatography

The dialysed crude ganglioside fraction was evaporated (lyophilized) and dissolved 1 volume of chloroform-methanol-water with a volume ratio of 60:30:4.5 per volume original tissue. A column (inner diameter 20 mm) was packed with Spherosil-DEAE-dextran, 0.2 volume of resin per volume of original tissue. The dialysed ganglioside extract was added slowly to the column and the column was then eluted with 10 bed volumes of chloroform-methanol-water (60:30:4.5, by volume). The monosialoganglioside fraction was eluted with 10 bed volumes of 0.02 M potassium acetate in methanol. The monosialoganglioside fraction was evaporated and desalted by dialysis against distilled water.

Purification of Fuc-GM1 by silica gel chromatography

For the chromatography 1 g of silica gel (latrobeads ®) was used for each g of original nervous tissue. The gel was suspended in chloroform-methanol (volume ratio 4:1) and poured into a glass column with a sintered glass filter and a diameter of 15–20 mm depending on the amount of gel. The ganglioside fraction was dissolved in 10 ml of chloroform-methanol-water (65:25:4, by volume) and applied to the column. It was eluted first with 15 ml of chloroform-methanol-water (65:25:4, by volume) for each g (weight/volume) of gel, which was collected in one fraction. The elution continued then with chloroform-methanol 2.5 M ammonia (60:40:9, by volume) and 5 ml fractions were sampled on a fraction collector. The elution was monitored by testing 10 μl of each fraction by high performance thin-layer chromatography with the same solvents as used for the column chromatography, chloroformmethanol-2 M ammonia (60:40:9) and the gangliosides were detected with resorcinol reagent. The fractions which contained Fuc-GM1 were pooled and evaporated to dryness.

The final purification of Fuc-GM1 was achieved by preparative thin-layer chromatography. Ganglioside (5 μmoles) was applied on a thin-layer plate (20×20 cm, 0.25 mm thick, Merck, AG., Darmstadt), which was developed for 60 min with chloroform-methanol-2.5 M ammonia at 21° C. After completed chromatography the plate was sprayed with 0.01% bromthymol blue in water and the Fuc-GM1 band was scraped off. The ganglioside was eluted from the gel with chloroform-methanol-water (30:60:20, by volume) and was added one drop of 0.1 M potassium hydroxide dissolved in methanol and evaporated to dryness. The pure ganglioside Fuc-GM1 was kept dry in a vacuum desiccator or was dissolved in a small volume of chloroform-methanol (2:1, by volume) and was kept in a teflon capped tube in the dark at +4° C.

EXAMPLE 2

Production of Monoclonal Antibodies Directed Against Fucosylsialosylgangliotetraose by Means of Ganglioside Fuc-GM1

The purified ganglioside Fuc-GM1 from Example 1 was adsorbed to acid-washed *Salmonella minnesota* bacteria before immunization according to the principle, described by Young, W.W. and collaborators (J. Exp. Med. 150, 1008–1019, 1979).

Balb/c mice, 6–8 weeks old, were immunized intravenously with 5 μg of ganglioside Fuc-GM1, adsorbed to 50 μg acid-washed *Salmonella minnesota* bacterial membranes, suspended in 100 μl of phosphate-buffered physiological saline, pH 7.4. A new immunization was performed after two weeks with the same dose of immunogen under identical conditions (booster dose).

Three days after the booster dose, the spleen cells taken from the immunized mice were fused with mouse Sp 2/0 myeloma cells. The resulting hybridomas were expanded, tested and cloned according to the protocol, devised by de St. Groth and Scheidegger (J. Immunol. Methods, 1–21, 1980). The culture medium was collected from each microtiter well with growing hybridomas to determine those secreting antibody specific for Fuc-GM1. The determination was performed in an ELISA system according to the following procedure: Fuc-GM1, 50 pmol dissolved in 50 μl of methanol, was added to the wells of a polyvinylmicrotiter plate and evaporated to dryness. The wells were incubated overnight with 100 μl of culture medium diluted 1:2 with 0.01 M phosphate buffered saline (0.14 M) (PBS), pH 7.5. After thorough washing with PBS the wells were incubated for 4 h with 100 μl of peroxydase (HRP)-conjugated rabbit anti-mouse immunoglobulin diluted 1/200 on PBS-1% bovine serum albumin (BSA). The absorbance at 450 nm was determined in a Titertek® microtiter scanner (Flow Laboratories, USA) after incubation for 5 min with 50 μl of substrate (0.1% orto-phenyldiamine in 0.1 M citrate buffer, pH 4.5, mixed with 0.3% $H_2O_2$). Hybrids were regarded as positive if the absorbance exceeded that of the mean medium blank by a 2-fold or more. Medium from positive hybrids was collected for further screening and the hybrids were frozen in liquid nitrogen.

Culture medium from hybrids positive in the initial ELISA screening against Fuc-GM1 was tested against normal human lymphocytes for cross-reactivity. Human lymphocytes (HuLy-c) were isolated by centrifugation on Lymphoprep® of blood from five donors of all ABH-blood groups, pooled and used as antigen in an ELISA-test as described by Lindholm et al. (Infect. Immun. 40, 570–576, 1983). Hybrids that produced antibodies cross-reacting with HuLy-c were not further expanded.

The Fuc-GM1positive/HuLy-c negative hybrids were cloned by limited dilution and expanded. The culture medium was collected and used for additional tests without further processing. The isotype of the antibodies produced by each clone was determined by single radial immunodiffusion in agarose containing isotype specific antimouse immunoglobulins.

The Fuc-GM1 positive/HuLy-c negative hybridomas were cloned and screened to determine those secreting antibody specific for Fuc-GM1. The determination was performed in a double antibody solid phase radioimmuno assay. Fuc-GM1 and a large number of different neutral glycolipids and gangliosides were dissolved in methanol and pipetted into the wells of microtiter plates. After evaporation of the solvents the antigen coated wells were incubated with the monoclonal antibodies. Bound antibody was detected with $^{125}I$-labelled antimouse immunoglobulin; $^{125}I$-antimouse IgM or $^{125}I$-antimouse IgaF(ab)$_2$ fragment. Each monoclonal antibody was tested against Fuc-GM1; a standard mixture of human brain gangliosides, normal lung tissue, neutral glycolipids and gangliosides.

The specificity of the monoclonal antibodies were also determined by thin-layer chromatographic immunostaining of the glycolipid antigens. The total neutral and acidic glycolipid fractions from a number of organs were separated on aluminia-backed high performance thin-layer plates (HPTLC) and incubated with the monoclonal antibodies of the Fuc-GM1 positive hybridomas, diluted with Tris buffer-1% BSA (0.05 M Tris, 0.14 M NaCl, pH 7.8, containing 10 g bovine serum albumin/l and 100 mg merthiolate/l). Bound monoclonal antibody was detected with $^{125}I$-labelled antimouse immunoglobulin and then exposing it to X-ray film for 12–24 h. When different monoclonal antibodies were tested on the same HPTLC-plate the antibodies were applied to the plate by soaking cellulose acetate strips in the antibody solution and covering one lane of the HPTLC-plate with the strip.

Only the antibodies which showed an exclusive specificity for Fuc-GM1 have been used in the subsequent studies.

EXAMPLE 3

Determination of Fucosylsialosylgangliosyltetraose Antigen in Lung Small Cell Carcinoma The same principle method was adapted as described in Example 1, but the method has been modified to be optimal for small tissue samples. Tissue, approx. 0.1 g, was homogenized together with 0.5 ml of water in a small conical tube tissue grinder with teflon pestle in an ice bath. After finished homogenization 1.6 ml of methanol and 0.8 ml of chloroform were added. After thorough mixing the tube was centrifuged at 800 xg for 10 min. The clear supernatant was transferred to a Kimax-tube with teflon cap. The sediment was suspended in 0.5 ml of water and then 1.6 ml of methanol and 0.8 ml of chloroform were added. Mixing and centrifugation were performed as before. The two supernatants were combined and water was added to give a final chloroform-methanol-water ratio 4:8:5.6 (by volume). After mixing the tube was centfigued at 100 xg for 5 min. The upper phase was transferred to a small round flask with ground neck and after addition of 0.1 volume of isobutanol, the supernatant was evaporated. The residue was the heated with 0.1 M sodium hydroxide in methanol for 1 h at room temperature.

After finished transesterification 4 ml of chloroform and 1 ml of methanol were added and the content was poured into a small column with 1 g of Sephadex G 25, packed in chloroform-methanol-water 60:30:4.5 (by volume). The eluate was slowly added to a column with 1.0 g of DEAE-Sepharose ® (Pharmacia Fine Chemicals, Uppsala, Sweden) in acetate form. After rinsing the column with 10 ml of methanol, the tumor antigen was eluted with 0.02 M potassium acetate in methanol. After evaporation and resolution in chloroform-methanol-water 65:25:4 (by volume) the simple monosialogangliosides were separated from the antigen fraction by elution with 15 column volumes of 65:25:4 (by volume), whereafter the antigen fraction was eluted with 10 volumes of chloroform-methanol-water 50:40:10 (by volume).

A portion of the antigen fraction was dissolved in methanol and 50 μl of extract was pipetted into the wells of a polyvinyl microtiter plate. Standard solutions of 0.5 to 5 pmol of pure Fuc-GM1 in methanol was added to other wells. The solvent was evaporated under a stream of nitrogen. To the unknown samples and standards 10–100 μg of monoclonal antibody, specific for Fuc-GM1 and produced as described in Example 2, dissolved in PBS/BSA was added. The samples were incubated for 1 h at room temperature. The wells were washed 3 times with PBS solution and then $^{125}$I-labelled antimouse-immunoglobulin was added and allowed to react for 3 hours. After repeated washing with PBS the wells with unknowns and standards were cut out from the microtiter plate and counted in the gamma counter. The concentration of fucosylsialosylgangliotetraosyl antigen of the unknowns were calculated from the standard curve of pure Fuc-GM1.

Under the described conditions Fuc-GM1 has been detected in 19/20 lung small cell carcinoma. The antigen has not been identified in other forms of lung carcinomas (squamous cell, large cell or adenocarcinoma) neither in carcinomas of mammary gland, stomach, colorectal mucosa, urinary bladder or uterus. Traces of the antigen has been shown in normal and carcinomatous pancreatic tissue.

EXAMPLE 4

Detection of Fucosylsialosylgangliotetraose Antigen in Blood Serum of Patients with Lung Small Cell Carcinoma The following procedure was used for the demonstration of the fucosylsialosylgangliotetraose antigen in blood serum or plasma. 1.0 ml of serum was slowly dropped into a small test tube with 4 ml of methanol under continuous agitation. Then 2 ml of chloroform was added and the content thoroughly mixed and centrifuged at 800 xg for 10 min. The clear supernatant was transferred to a new tube and the solvent evaporated in a stream of nitrogen under gentle warning on a water bath of 40° C. The residue was dissolved in 5 ml of chloroform-methanol-water 60:25:4 (by volume) and put into a small column (inner diameter 8–10 mm) with 1 g of silica gel (Silica Gel 60, 230–400 mesh, Merck AG, Darmstadt, FRG). The column was eluted with 20 ml of chloroform-methanol-water 65:25:4, (by volume), and then the tumor antigen was eluted with 10 ml of chloroform-methanol-water 50:40:10 (by volume). After evaporation, dialysis for two days against water, and lyophilization, the residue was dissolved in 5 ml of chloroform-methanol-water 60:30:4.5 (by volume) and added slowly to a small column with 1 g of DEAE-Sepharose in acetate form. The column was eluted with 10 ml of methanol and then the tumor antigen was eluted with 10 ml of 0.02 M potassium acetate in methanol. The salt was removed by dialysis and after evaporation the residue was dissolved in a small volume of methanol.

The concentration of tumor antigen was determined with a double solid phase antibody method, at which the antigen was adsorbed to the solid phase and determined with the specific monoclonal antibody (Example 2) and antimouse-immunoglobulin. Fuc-GM1 (20 pmol) and the purified antigen fraction of unknown serum samples were dissolved in methanol and serial dilutions of them ($\frac{1}{2}$-1/2048) were pipetted in the wells of polyvinyl microtiter plates (Flow Laboratories art.nr. 77-173-05) and were evaporated. Unspecific binding of the wells was blocked with 20 μl of 1% BSA in PBS and then 50 μl of specific monoclonal antibody, diluted in 1% BSA in PBS, was added. After incubation for 4 hours, the wells were rinsed 3 times with 200 μl of PBS. After the rinsing rabbit antimouse immunoglobulin labelled with $^{125}$I, peroxydase or β-galactosidase was added. Measurement of the antigen amount was performed in a gamma counter or after addition of enzyme substrate (ortophenyl diamine, see Example 2), or methylumbelliferyl-β-galactoside in citrate buffer, pH 4.2) reading of the absorbance in a spectrometer or spectrofluorimeter, respectively. The concentration of cancer antigen in blood serum was calculated from the standard curve of Fuc-GM1.

Under the conditions specified above, the antigen was only detected in blood serum of patients with lung small cell carcinoma.

EXAMPLE 5

Cytolytic Effect on Tumor Cells Expressing the Fuc-GM1 Antigen by Monoclonal Antibodies Against Fuc-GM1 in Conjunction with Macrophages The ability of specific monoclonal antibodies against Fuc-GM1 to kill human tumor cells expressing the Fuc-GM1 antigen was tested in vitro using the antibody-dependent macrophage/monocyte mediated cytotoxicity test (ADMMC).

The specific example described here involved the use of a Fuc-GM1 specific mouse monoclonal antibody (designated F12) prepared as described in Example 2 above, and the Fuc-GM1-containing hepatoma tumor cell line H4-11-E1 (American Type Culture Collection, Rockville, Md) and mouse peritoneal macrophages as target and effector cells, respectively. The F12 monoclonal antibody, prepared and shown to be specific for Fuc-GM1 as described in Example 2 above, was produced for this experiment by injecting F12 hybridoma cells into pristane (2,6,10,14-tetramethylpentadecaene, Aldrich Chemical Co, W Germany) treated normal Balb/c mice. The F12 monoclonal antibody was purified from ascites fluid collected from these mice. After precipitation of ascites fluid with 40% saturated ammonium sulphate, the monoclonal antibody was dialysed against PBS and then adsorbed on a Protein A-Sepharose (Pharmacia AB, Uppsala, Sweden) column and eluted as described by Lindmark (J Immunol Methods, 62:1-13, 1983). Following neutralization with sodium hydroxide (NaOH), the monoclonal antibody was dialysed against PBS, and the immunoglobulin preparation was determined to be pure by agarose gel electrophoresis and quantified by protein determination. The monoclonal antibody was stored at $-20°$ C. until use and was then tested in different concentrations (dilutions prepared in PBS). The hepatoma cell line, H4-11-E1 was cultured in Iscove's medium supplemented with 10% fetal calf serum, and the cells trypsinized, washed and suspended in PBS. This cell line contains large amounts of membrane-associated Fuc-GM1 as determined by the methods described in Example 1 and by immunofluorescence studies using the F12 monoclonal antibody. Mouse peritoneal macrophages were prepared by eliciting peritoneal exudate cells (PEC) by injection of 1.0 ml thioglycollate broth (Difco Laboratories, Detroit, Mi) intraperitoneally into nude mice and collecting the peritoneal cells by peritoneal lavage with 5 ml of sterile sucrose (11.6%) solution 3-4 days later. PEC were washed in PBS and counted in a hemacytometer, and the concentration of cells adjusted to $1 \times 10^6$/ml. One hundred $\mu$l ($1 \times 10^5$ cells) of the cell suspension was then aliquoted into 96-well flat-bottom plates (Falcon Plastics, Oxnard, Ca) and incubated for 1-2 h at 37° C. in a $CO_2$ humidified incubator to allow for cell adherence. Non-adherent cells were washed away by aspirating the medium and rinsing each well with PBS 2 times. This procedure yielded a confluent monolayer of adherent cells. Adherent PEC were determined to be 90% macrophage by non-specific esterase staining (kit available from Sigma Diagnostics).

The ADMMC assay was performed in the following way. To each well containing the thioglycollate-elicited macrophages (prepared as described above) were added $4 \times 10^4$ tumor target cells in the presence or absence of purified monoclonal antibody. Serial dilutions of the monoclonal antibody to provide concentrations of 100, 10, 1, 0.1, 0.01, and 0.001 $\mu$g/ml of monoclonal antibody, were made in culture medium and added to test wells containing (6-$^3$H) thymidine (Amersham, England) labelled H4-11-E1 cells and the plates incubated at 37° C. in a $CO_2$ humidified incubator for approx. 40 h. After incubation, tumor cell lysis was measured by release of label into the medium and calculated as follows: Percent cytotoxicity = (experimental release of CPM)—(spontaneous release of CPM) / (maximal release of CPM)—(spontaneous release of CPM)$\times 100$. Supernatants were collected from triplicate wells and counted in a $\beta$-counter after diluting samples in a scintillation cocktail (Instagel®, Packard, Sweden). Maximum release of label was determined by solubilization of cells in 2% SDS.

Using the ADMMC method and the conditions described the results shown below were obtained in a typical experiment. The data clearly show that a specific monoclonal antibody against Fuc-GM1 was highly efficacious in conjunction with macrophages in killing and lysing Fuc-GM1 containing tumor cells in vitro.

| F12 monoclonal antibody concentration, $\mu$g/ml | % tumor cell lysis |
| --- | --- |
| 100 | 100 |
| 10 | 100 |
| 1 | 86 |
| 0.1 | 45 |
| 0.01 | 28 |
| 0.001 | 33 |
| None (medium only) | 30 |
| 100 $\mu$g/ml but no macrophages | 9 |

EXAMPLE 6

Treatment Effect in Vivo (Suppression of Tumor Development) by Fuc-GM1 Specific Monoclonal Antibody Against Fuc-GM1-Expressing Tumor Cells in the Nude Mouse Model We examined the F12 mouse monoclonal antibody against Fuc-GM1, which had shown ability to kill and lyse Fuc-GM1 expressing tumor cells in vitro in conjunction with macrophages as described in Example 5 above for its ability to also suppress tumor development in nude mice in vivo.

The monoclonal antibody F12 was prepared and purified as described in detail in Example 5, and the Fuc-GM1-containing tumor cell line H4-11-E1 was also propagated and cell suspensions prepared as described in Example 5. Thymus-deficient nude mice (nu/nu of C57B1/6 background), 5-8 weeks old, were purchased from Bomholtgaard, Ry, Denmark. Nude mice were housed under pathogen-free conditions in a laminar flow hood in sterilized cages with autoclaved food and water provided ad libitum. All animals used were of the same sex, male.

Tumors were induced by injecting the mice subcutaneously with $2 \times 10^6$ H4-11-E1 cells suspended in 0.1 ml of PBS. Inoculation of tumor cells was made at 2 opposite localizations on the dorsal hind quarters, and the mice were divided into 3 groups with 10 animals in each group. Mice in 2 of these groups then received daily injections of monoclonal antibody F12 intraperitoneally for 20 days (group A, 0.2 mg monoclonal antibody/injection; and group B, 0.02 mg/injection). The mice of the third group, group C, served as controls of sham-treated tumor growth and were injected daily for 20 days with PBS containing no monoclonal antibody. The incidence of tumor was recorded twice weekly throughout the experiment as the occurrence of tumors at the sites of tumor cell inoculation. Following a 50 day observation period, i.e. 30 days after the last monoclonal antibody or PBS injection, mice were sacrificed.

The figure below summarizes the treatment effects achieved in this experiment. It is evident that with both of the F12 monoclonal antibody treatment dosages tested there was a significant reduction of tumor development as compared to the sham-treated (PBS injected) control group. In fact, with the higher dosage of monoclonal antibody treatment (group A) there was a complete abolition of tumor development. At the time for completion of the experiment the tumor rate (percent palpable tumors out of inoculated tumor sites) in the 3 groups were as follows: Group A, 0%; Group B, 18%; and Group C 55%.

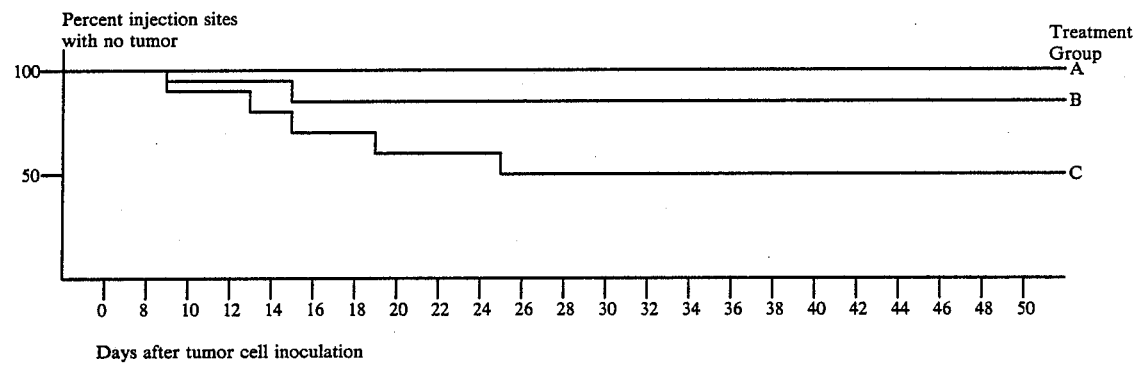

Days after tumor cell inoculation

EXAMPLE 7

Immunohistochemical Detection of Fucosylsialosylgangliotetraose Antigen in Tissue Specimens of Patients with Lung Small Cell Carcinoma An immunofluorescence method involving a highly specific mouse monoclonal antibody (designated F12) against Fuc-GM1 was used to study the distribution of the Fuc-GM1 antigen in different types of human lung cancer and normal tissues. The monoclonal antibody was prepared as described in Example 2 above. The antibody was concentrated by precipitation of F12 hybridoma culture supernate with 50% saturated ammonium sulphate solution, whereafter the precipitate was redissolved in 1/10 of the starting volume and dialysed against PBS. Tissue specimens obtained at autopsy from patients died from various forms of lung cancer were fixed in 4% formaldehyde in PBS and then frozen in liquid nitrogen and stored at −70° C. Biopsy specimens and some autopsy specimens were directly frozen without previous formaldehyde fixation. Cryostate sections, 4–6 μm thick, were put on glass slides precoated with 0.3% gelatin. After drying by air the cryostate sections were fixed with 5% paraformaldehyde in PBS for 30 min at room temperature followed by treatment with 7.5% sucrose in PBS at 4° C. overnight. The section was then incubated with the F12 Fuc-GM1 specific monoclonal antibody for 30 min at room temperature followed by consecutive incubations for 30 min each with fluoresceine isothiocyanate-conjugated (FITC) rabbit antimouse immunoglobulin (Dako, Dakopatts, Copenhagen, Denmark) and FITC-conjugated swine antirabbit immunoglobulin (Dako), each reagent in a concentration found to be optimal as determined by checker board titrations. Each of the incubation steps during the staining procedure was followed by washing for 15 min with three changes of PBS. Slides were finally mounted with 87% (w/v) glycerol in PBS. The slides were examined for specific fluorescence by microscopy under fluorescent light in a "blinded" fashion.

With this method 19 of 21 cases of small cell lung cancer specimens were specifically stained for Fuc-GM1 with the F12 monoclonal antibody as compared to 2 of 10 cases of squamous epithelial cell lung cancer and 1 of 5 large cell lung cancer specimens. Specimens of lung adenocarcinoma (8 cases) and bronchial carcinoid (3 cases) were all negative, as were 2 examined cases of neuroblastoma. No Fuc-GM1 antigen could be detected by this method in normal lung or bronchial tissues. All other normal tissues tested were also negative except sparsely distributed clusters of stained small round cells in thymus, spleen and lamina propria of the small intestine and intramural ganglionic cells of the small intestine and islet cells of the pancreas. These findings support the view that Fuc-GM1 is highly associated with small cell cancer of the lung and they demonstrate that this tumor-associated antigen can be detected with high sensitivity and specificity with an immuno- fluorescence method based on the use of specific monoclonal antibody against Fuc-GM1.

We claim:

1. A method of diagnosing or monitoring a patient suspected of having small cell carcinoma of the lung comprising:
    (a) the determination in specimens of a specific cancer-associated antigen of carbohydrate nature, fucosylsialosylgangliotetraose (Fuc$\alpha$1-2Gal$\beta$1-3 GalNAc $\beta$1-4(NeuAc$\alpha$2-3) Gal$\beta$1-4 Glc),
    (b) relating the presence of said antigen to the presence of said carcinoma in said patient.

2. The method of claim 1 wherein the antigen is naturally bound to a lipid in the form of a glycolipid, or bound to a peptide or protein in the form of a glycopeptide or glycoprotein.

3. The method of claim 1 wherein the antigen is demonstrated in a tissue or body fluid specimen after lipid extraction and chromatographic purification by binding to a solid phase and incubation with fixation to a specific antibody against the antigen.

4. The method of claim 3 wherein the specific antibody is labelled with a radioisotope, an enzyme or a fluorescent probe.

5. The method of claim 3 wherein the binding of the specific antibody is demonstrated through a second antibody, directed against the first antibody, and labelled with a radioisotope, an enzyme or a fluorescent probe.

6. The method of claim 1 wherein the antigen is demonstrated in tissue sections or cell smears by immunohistochemical methods through contacting the specimen with a specific antibody against the antigen.

7. The method of claim 6 wherein the binding of the specific antibody is demonstrated through a second antibody, directed against the first antibody, and labelled with a radioisotope, an enzyme or a fluorescent probe.

8. The method of claim 6 wherein the specific antibody is labelled with a radioisotope, an enzyme or a fluorescent probe.

* * * * *